United States Patent [19]

Frey et al.

[11] Patent Number: 4,860,750

[45] Date of Patent: Aug. 29, 1989

[54] SIDELOCK PACER LEAD CONNECTOR

[75] Inventors: Michael L. Frey, Alvin, Tex.; Gunter Becker, Sterling Heights, Mich.

[73] Assignee: Intermedics Inc., Angleton, Tex.

[21] Appl. No.: 853,195

[22] Filed: Apr. 17, 1986

[51] Int. Cl.⁴ .............................................. A61N 1/00
[52] U.S. Cl. ................................................ 128/419 P
[58] Field of Search ............ 128/419 E, 419 F, 419 P, 128/419 PS, 419 R; 439/863, 864

[56] References Cited

U.S. PATENT DOCUMENTS

| | | |
|---|---|---|
| 839,817 | 1/1907 | Decker . |
| 3,042,896 | 7/1962 | Doktor . |
| 3,760,332 | 9/1973 | Berkovits et al. . |
| 3,824,556 | 7/1974 | Berkovits et al. . |
| 3,845,457 | 10/1974 | Reimer ................................ 439/864 |
| 3,963,305 | 6/1976 | Doktor . |
| 4,112,953 | 9/1978 | Shanker et al. . |
| 4,180,078 | 12/1979 | Anderson .......................... 128/419 P |
| 4,182,345 | 1/1980 | Grose ................................ 128/419 P |
| 4,202,592 | 5/1980 | Rullier et al. . |
| 4,226,244 | 10/1980 | Coury et al. ...................... 128/419 P |
| 4,259,962 | 4/1981 | Peers-Trevarton . |
| 4,278,093 | 7/1981 | Lafortune et al. . |
| 4,347,849 | 9/1982 | Congdon . |
| 4,445,511 | 5/1984 | Cowdery et al. . |
| 4,461,194 | 7/1984 | Moore ................................ 128/419 P |

Primary Examiner—Max Hindenburg
Attorney, Agent, or Firm—Russell J. Egan

[57] ABSTRACT

A connector for a lead of a tissue stimulator such as a cardiac pacer uses a wedging element to fix the lead against inadvertent withdrawal from the pacer header. A wedge member is received in a channel which intersects a bore in the header in which the lead is inserted for connection with a pulse generator. When the wedging member is pressed into its channel, as by simple finger pressure, it engages the lead off-axis, e.g. along a tangent, and forces the lead into tight engagement with the sidewall of the header bore. A present embodiment is adapted for use with a lead which has a deformable covering. The wedge member has a concavity formed therein within which the lead seats. A first end of the wedge member has an upraised portion which is hump-shaped. This upraised portion first cams the lead into engagement with the bore sidewall, and then passes beyond the lead by deforming the lead covering. The lead then seats in the concavity. This serves to not only lock the lead within the bore, but also prevent the wedge member from being dislodged, since it is in turn now located in place by the lead. The wedge member is preferably located on a lateral side of the header so that it is readily accessible for use. Embodiments are disclosed for use with single bore as well as double bore headers.

24 Claims, 3 Drawing Sheets

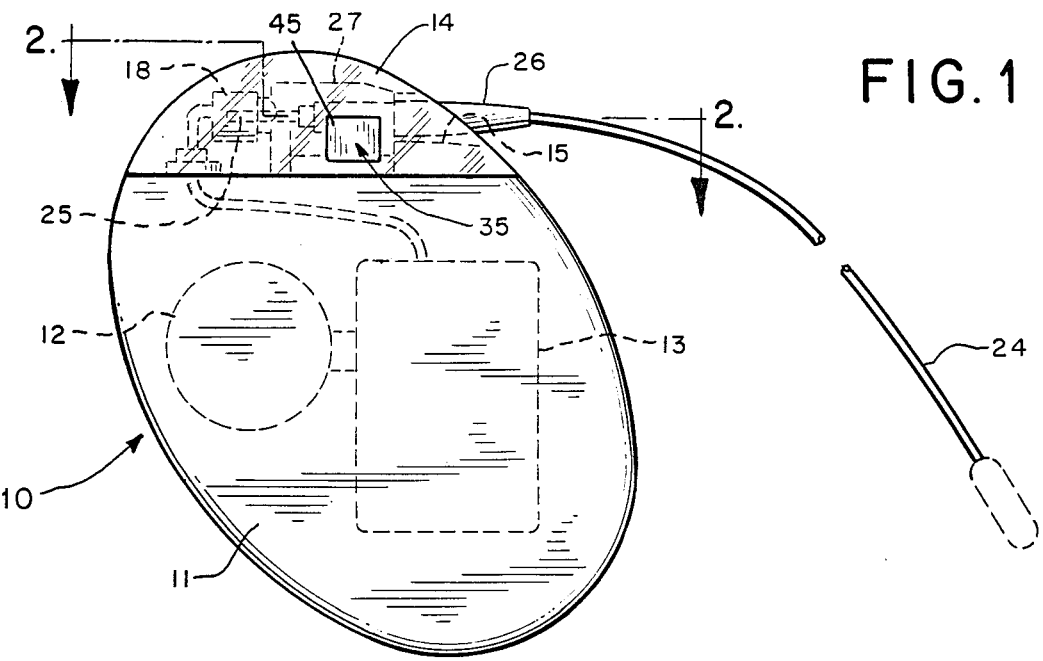
FIG. 1
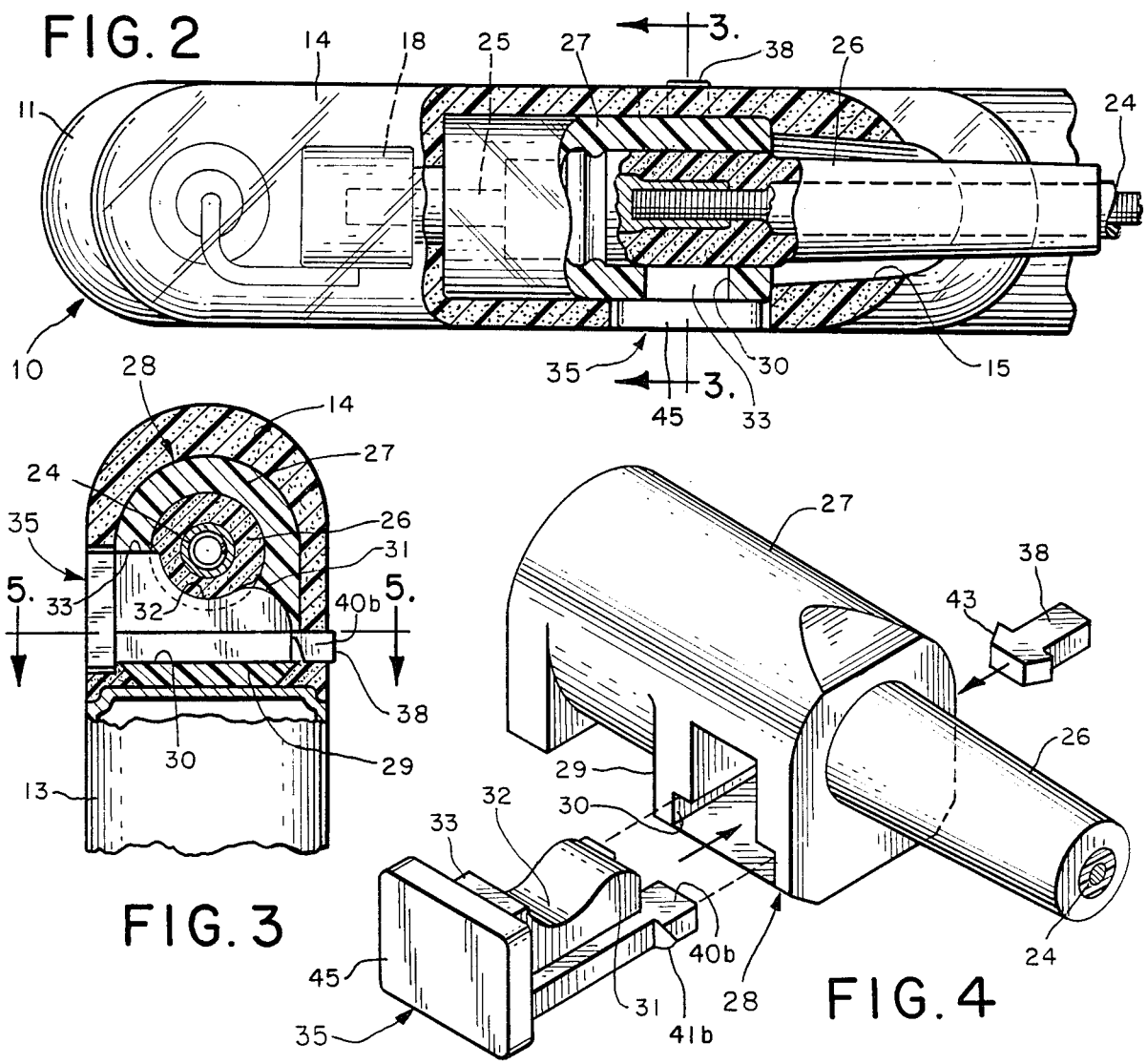

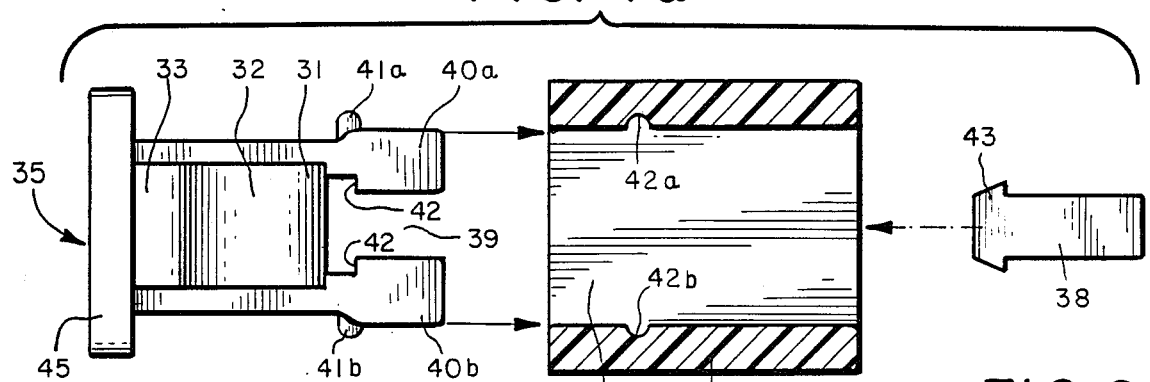
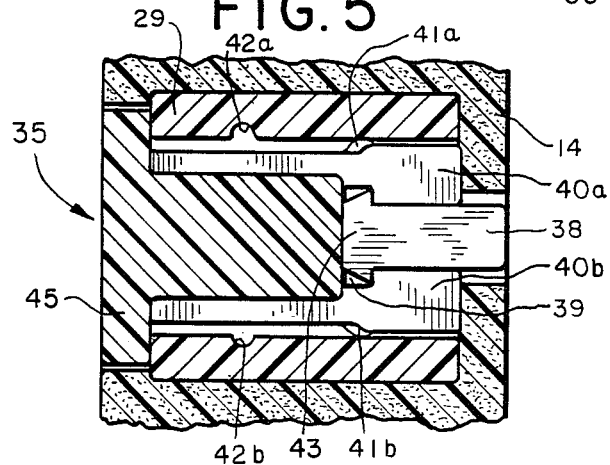
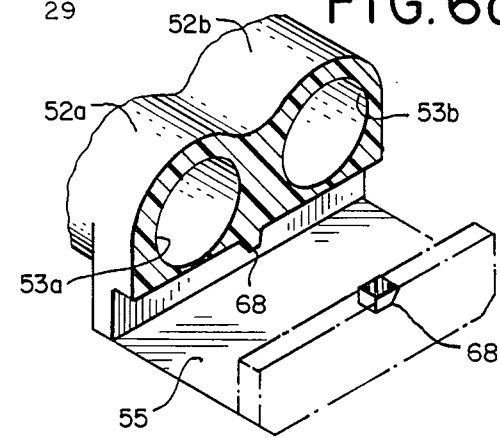
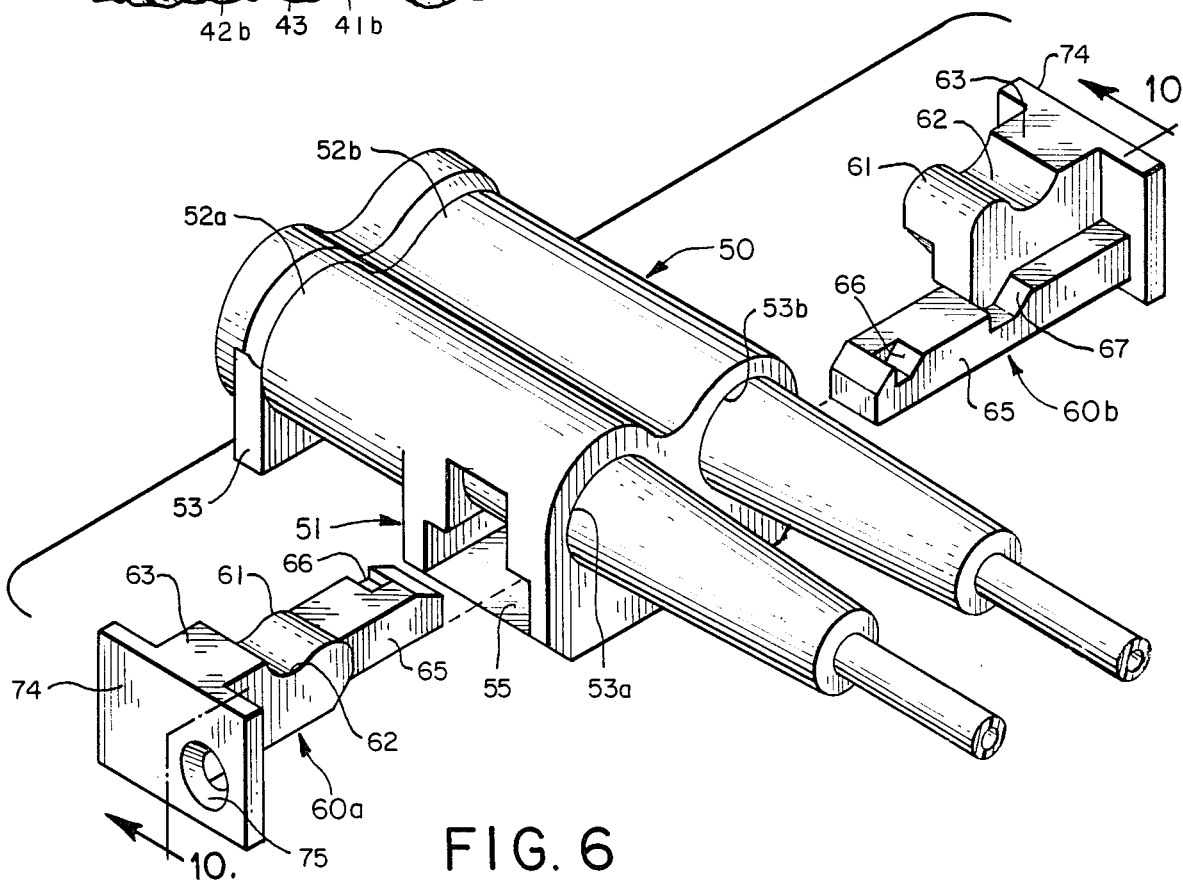

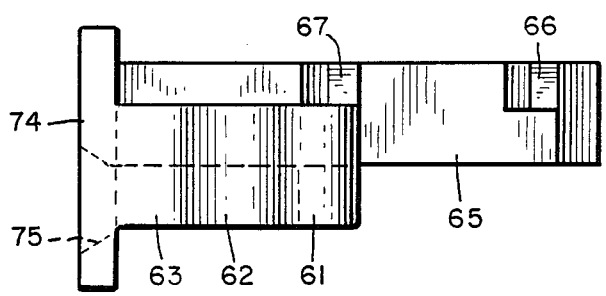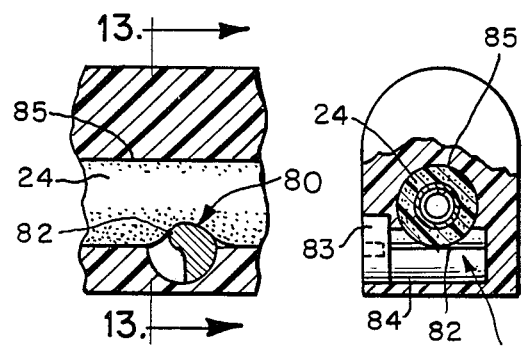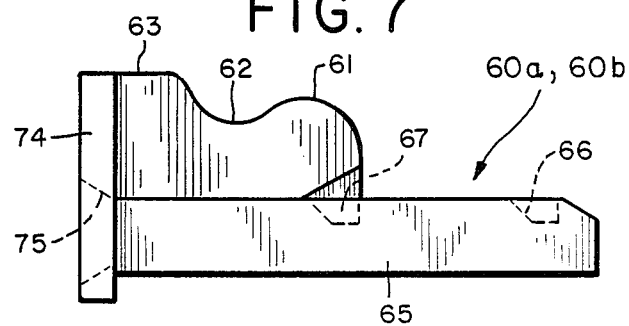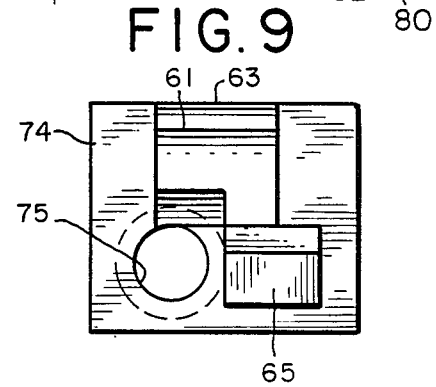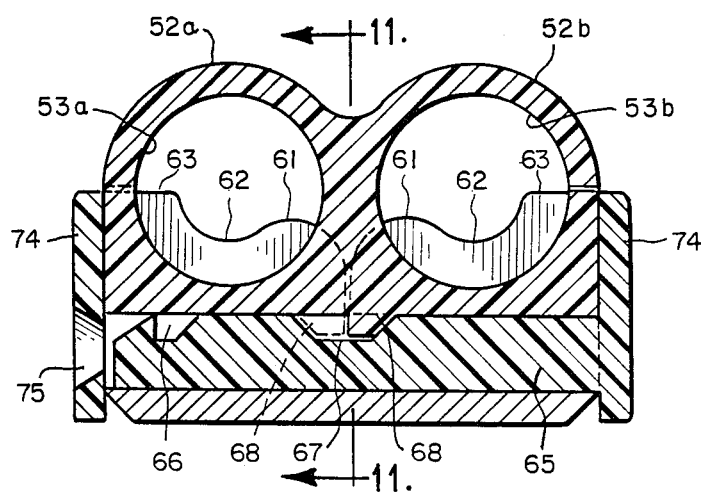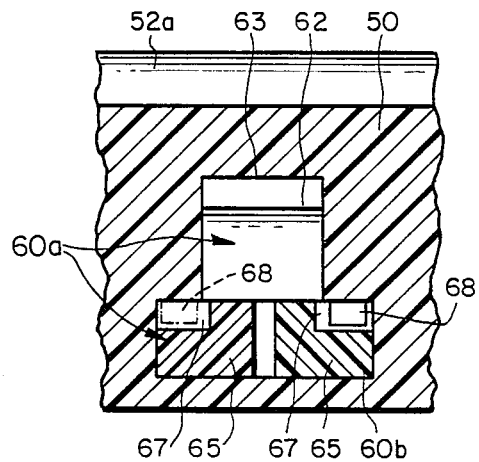

SIDELOCK PACER LEAD CONNECTOR

FIELD OF THE INVENTION

This invention relates to connectors for coupling a lead for a tissue stimulating device, such as a cardiac pacer, to a pacer pulse generator, and more particularly to a mechanical connector which prevents inadvertent decoupling of the pacer lead.

BACKGROUND OF THE INVENTION

Electronic pacers (pacemakers) are used to artificially stimulate tissue such as the heart muscle with a pulsed electrical signal in order to correct or modify its rhythm. Body-implantable pacers are quite common, and generally comprise a small self-contained housing or can which encloses a source of electrical energy (a battery) and an electronic apparatus for producing electrical impulses at appropriate intervals. It is implanted by making a subcutaneous cavity in which the housing is positioned. The housing is made with a thin width to this end, so that it makes as small a bulge as possible on the overlying skin. An electrode at one end of a catheter is implanted in the heart muscle. The other end of the catheter has a lead formed thereon which is electrically coupled to the pacer pulse generator to complete the pacer circuit.

It is important that the catheter lead is safely secured to the pacer to prevent it from being inadvertently decoupled. Since pacers must often be removed and replaced as a complete unit without need of disturbing the electrode, the lead connection must also be readily disconnectable.

It has been common in the art to accomplish this connection by inserting an exposed terminal pin of the lead into an electrical terminal located at the inboard end of a cylindrical bore in the neck of the pacer, which may be a header formed on the pacer. The lead is then fixed in place by use of a setscrew, which extends through a tapped hole through the side of the header into the bore.

This conventional technique for securing the lead to the pacer has significant drawbacks. The manipulation of an extremely small screw through the use of a wrench or other tool can be difficult and time-consuming. Fairly elaborate steps must additionally be taken to secure the setscrew and seal the tapped hole of the setscrew against body fluids. To this end, surgical cement or some other sealing compound is typically introduced into the tapped hole to fix the set-screw in place and seal the hole. Furthermore, removal of the pacer is complicated by the need to remove the cement from the hole and setscrew.

Alternatives to the use of the foregoing setscrew technique have been developed, such as shown in U.S. Pat. Nos. 4,259,962 and 4,112,953, for example. These alternatives substantially rely upon the lead being tightly gripped within the bore by resilient strands, flanges and the like. The leads can be removed by exerting sufficient axial force to pull them out.

In the first instance, it is undesirable to have a surgeon yanking on a pacer lead to pull it out from the pacer, particularly when the electrode is embedded in the heart. This may also damage the lead as well as deform the coupling mechanism. Secondly, the lead may pull free from the pacer after implantation if sufficient force is applied which exceeds the strength of the connection.

SUMMARY OF THE INVENTION

It is a principal objective of the present invention to provide an improved connector for a lead of a tissue stimulator, such as a cardiac pacer, which is easily manipulated by finger pressure to lock a lead in place in the pacer, which substantially eliminates the need for any screw drivers, wrenches or other special implements for use with the connector, which provides a positive lock for the lead that prevents inadvertent decoupling, and which is readily accessible to the surgeon for repeatedly locking and unlocking leads to the pacer.

To this end, the invention comprises a locking device for fixing the lead end of a catheter against withdrawal from a bore in a pacer header which uses a wedge member to wedge the lead end in place within the bore. The wedge member is received in a channel formed in the header which intersects the bore within which the lead end is located. When the wedge member is pressed inboard (into the channel), as by simple finger pressure, the wedge member engages a side of the lead end off-axis, e.g. roughly along a tangent. This presses the lead against the opposite sidewall of the bore and firmly wedges the lead in place.

The channel for the wedge member preferably extends completely through the header. When it is desired to remove the lead end from the pacer, the wedge is simply pushed outboard (out of the channel) by use of a convenient implement inserted into the opposite end of the channel. This frees the lead end.

One present embodiment of the invention is adapted for a pacer header having a single bore, i.e. one lead. It is used with a lead end having a circular cross section and a resilient covering over the lead end. The bore is sized slightly larger in diameter than the lead end for a snug fit with the lead end, and can advantageously receive leads having differing diameters, within a small range.

The wedge member has a lead engaging surface comprised of a first upraised portion which is hump-shaped in appearance, a concave portion, and a second upraised portion. A channel for the wedge member is formed in the header and extends completely therethrough. This channel is orthogonal to the lead bore, and intersects the bore along an off-axis chordal portion, i.e. roughly along a tangent.

The wedge member is slidable in the channel between a first (unlocked) position, wherein a portion of the wedge member extends outboard beyond the adjacent side of the header/pacer housing, to a second (locked) position wherein the lead end is seated in the concave portion of the wedge member. The outboard end of the wedge member is flush with the adjacent side of the header/pacer housing in this second position.

In locking the lead end, the upraised portion of the wedge member engages the side of the lead and cams it into a tight frictional engagement with the opposite bore sidewall. As the wedge member is pressed further into the channel, the first upraised portion deforms the resilient covering of the lead as it passes from one side of the lead to the other. The lead covering partially regains its shape within the concave portion of the wedge member once the first upraised portion has passed. It is still firmly pressed against the sidewall, however. The wedge member is thereby fixed in place within the channel by virtue of the upraised portions located on either side of the compressed lead end.

Both the lead and the wedge member are thus readily fixed against removal in a positive lock by the simple step of pressing in the wedge member with the fingers. No special tool is required.

If desired, the wedge member can be further secured within the channel. To this end, the wedge member has a pair of legs formed at its inboard end separted by a small cavity. A small pin is inserted within this cavity once the wedge member is in the locked position, and serves to assure that the legs remain spread apart against the channel sidewalls. The pin has an enlarged head which engages within the cavity to prevent it from becoming dislodged.

The lead end is readily released from the bore by simply pushing the wedge member back out of the channel. This is done by taking any convenient implement and inserting it into the far end of the channel, i.e. the channel end nearest the wedge legs. The wedge member, including the captive pin, is then pushed outboard to free the lead end.

A second embodiment of the invention is adapted for use with a pacer header having two side-by-side bores, i.e. which is adapted for two leads. A single channel is formed through the header which intersects both of the leader bores roughly along a tangent. Two identical wedge members are used in this embodiment, each being inserted in opposite ends of the channel. Each wedge member fixes a respective lead in place in its bore.

Each of the wedge members has a lead engaging surface which his contoured as in the first embodiment. A pair of small bosses located in the channel engage with detents on the wedge members to secure the wedge members against unintended removal once locked.

The outboard ends of the two wedge members are flush with the header/pacer housing sides when in the locked position. A small aperture is provided in each of these outboard ends through which an implement can be inserted to contact the inboard end of the other member. The member so contacted can then be pressed outboard with the implement to free its respective lead end.

While the two foregoing embodiments relate to a lead connector using a wedge member that is pressed into a channel for securing a lead, a wedge member that is rotated in the channel is also within the scope of this invention. For instance, such a wedge member would have a cam surface that is rotated into engagement with a lead to thereby fix the lead in place.

The foregoing features and advantages of the present invention will be further understood upon consideration of the following detailed description of the invention taken in conjunction with the accompanying drawings, in which:

BRIEF DESCRIPTION OF THE DRAWINGS

FIG. 1 is an elevational view of a pacer incorporating a first embodiment of the invention;

FIG. 2 is a sectional view along line 2—2 of FIG. 1;

FIG. 3 is a sectional view along line 3—3 of FIG. 2;

FIG. 4 is an enlarged view of the wedge member and housing;

FIG. 4a is a top plan view of the arrangement of FIG. 4 with the channel for the wedge member in section;

FIG. 5 is a sectional view along line 5—5 of FIG. 3;

FIG. 6 is a view similar to that of FIG. 4 showing a second embodiment of the invention;

FIG. 6a is a cut-away view of the housing of FIG. 6 detailing the channel for the wedge members;

FIG. 7 is an enlarged elevational view of a wedge member of the second embodiment;

FIG. 8 is a top plan view of the wedge member of FIG. 7;

FIG. 9 is an end view of the wedge member of FIG. 7, as viewed from the right-hand side of that figure;

FIG. 10 is a sectional view along line 10—10 of FIG. 6 with the wedge members inserted in the channel;

FIG. 11 is a sectional view along line 11—11 of FIG. 10;

FIG. 12 is a diagrammatic view of another embodiment employing a rotatable wedge member; and FIG. 13 is a diagrammatic sectional view along line 13—13 of FIG. 12.

DETAILED DESCRIPTION OF EMBODIMENTS OF THE INVENTION

Two presently preferred embodiments of the invention are described hereafter. The first embodiment (FIGS. 1–5) is adapted for use with a pacer header that receives a single lead. The second embodiment (FIGS. 6–11) is adapted for use with a dual chamber header that receives two leads, i.e. for two area cardiac stimulation.

Referring now to FIG. 1 and the first embodiment, a self-contained body implantable pacer 10 has a housing or can 11 which contains a source of electrical energy, i.e. a battery 12, and a device 13 for generating a pulse. A header 14 having a single chamber or bore 15 is formed on the housing. An electrical terminal 18 is located at the inboard end of the bore 15, and is electrically connected to the pulse generator 13.

The pacer can is made of a corrosion-resistant metal such as titanium. It is sealed after the battery 12, pulse generator 13 and associated circuitry are placed therein. The header 14 is made of an epoxy resin or similar thermosetting polymer material which is formed in situ over the other components in the header body, e.g. the electrical terminal 18. These other components in the header 14 are thereby directly supported by the cured resin which also surrounds and insulates all of the components. Use of a transparent resin further allows observation of the lead connection procedure. It may be noted that there are other techniques for forming the header 14, such as molding it separate from the housing 11, adding the other header components after molding, etc.

It will be understood that the foregoing elements and construction of the pacer are conventional and well known to those possessing skill in this art. Further detail concerning the general structure and operation of the pacer will accordingly be omitted herein.

A flexible catheter 24 extends between the heart and the pacer. It has an electrode (diagrammatically illustrated) at one end which is implanted directly in the cardiac muscle. The other end of the catheter is the lead end which terminates in a male connector pin 25. The pin 25 is inserted into the terminal 18 of the pacer. The lead end of the catheter has a covering 26 of silicone rubber which is both resilient and nonconductive. One or more wires of the catheter which extend between the electrode and pin 25 are enclosed within a covering or sheath of silicone or polyurethane. The particular catheter illustrated is a unipolar type catheter.

The lead end of the catheter 24 is received in the bore 15 of the header 14 in order to insert the pin 25 into the terminal 18. The bore 15 is formed by a tube 27 which is made of a rigid clear plastic. The tube 27 has an internal diameter which is slightly greater than the exterior diameter of the catheter 24. The catheter 24 thus snuggly fits within the tube 27.

The tube 27 is part of a housing 28 for the lead locking mechanism (e.g. FIG. 4). This housing 28 comprises the tube 27 and a base 29, which is also made of the same rigid clear plastic. The base 29 has a channel 30 formed therein which is orthogonal to the longitudinal axis of the tube 27. This channel 30 extends completely through the base 29, and intersects the tube off-axis. In this embodiment, the intersection is roughly along a tangent to the tube 27. (For purposes of clarity, such a tangential intersection describes the overlapping of the channel 30 with the tube 27 along an off-axis chordal portion of the tube.)

Viewing this arrangement from the perspective of FIGS. 1 and 2, the tube 27 extends along the minor axis of the pacer, and is located on top of the channel 30. The latter extends through the thickness of the header 14, i.e. from the front side to the back side of the header/pacer (bottom to top of FIG. 2).

The entire housing 28 is formed by molding in a single operation. It is then assembled with the other components of the header 14 and in situ molded into the header.

A wedge member 35 is received in the channel 30, and is used to fix the lead end in place within the tube 27. In this regard, it will be noted that the side of the lead end extends within the channel 30 when pin 25 is coupled with the terminal 18. When the wedge member 35 is pushed into the channel 30, it engages this side of the lead and presses the lead against the sidewall of the tube 27. The lead end is thereupon wedged in place, and cannot be removed from the header 14 without unusual force.

More specifically, and with particular reference to FIGS. 3–5, wedge member 35 has a contoured lead engaging surface having a first upraised portion 31 which is somewhat hump-shaped. This is followed by a concave depression 32 within which the lead seats, and a second upraised portion 33. The hump-shaped portion is adjacent the inboard end of the wedge member 35, i.e. the end which is initially inserted into the channel 30.

This hump-shaped portion 31 acts to cam the lead upwardly and into engagement with the tube 27 sidewall. Since the lead has a resilient cover 26, the cover is deformed by this camming action (i.e. the catheter is squashed) when the wedge member is being inserted. After the hump-shaped portion passes beyond the center of the lead, the lead partially regains its shape and seats in the concave portion 32. The lead is still under compression when so seated, however. In this embodiment, the hump-shaped portion has a radius of about 0.035 m, with a maximum height (channel floor to peak of hump) of about 0.072 m. The concave portion has a radius of curvature of about 0.052 m.

The wedge member 35 is in turn fixed in place by the compressed lead. Once seated in the concave portion 32, upraised portions 31,33 are located on either side of the lead (FIG. 3). The wedge member 35 therefore cannot move.

To further assure that the wedge member 35 does not become inadvertently dislodged from the channel and the lead end thereby freed, a small pin 38 is inserted into a cavity 39 formed in the inboard end of the wedge member 35 (FIGS. 4a and 5). Insertion of the pin 38 serves to assure that a pair of legs 40a, 40b formed on opposite sides of the cavity remain spread apart and tightly engaged with the channel sidewalls.

It will be noted that each leg 40a, 40b has a respective boss 41a, 41b formed thereon. It is these bosses 41a, 41b which actually engage with the channel sidewall. The bosses 40a, 40b also engage in corresponding detents 42a, 42b formed in the adjacent sidewalls of the channel 30 when the wedge member is initially inserted therein. This serves to locate the wedge member 35 in the channel so that it does not become loose prior to locking of the lead.

Pin 38 has a head 43 which is received in a widened portion of the cavity 39. The head 43 engages with an interior shoulder 42 at the outboard end of the widened cavity portion to prevent the pin from being dislodged once inserted. A pair of tweezers is useful for inserting the pin 38 in place. It will be noted in this regard that the cavity 39 is readily accessible from the back side of the header, since the inboard side of the wedge member 35 (i.e. the legs 40a, 40b) is substantially flush with the exterior of the header.

The outboard end of the wedge member 35 has a head 45 formed thereon. The head 45 abuts against the outside of the opening of the channel 30, and is substantially flush with the exterior of the header when the wedge member 35 is fully inserted (a recessed area is provided in the epoxy header to this end).

In use, the wedge member 35 is partially inserted in the channel 30. The surgeon then inserts the lead end into the bore 15 of the header 14 and couples the pin 25 with the terminal 18. The header 14 is then grasped between the thumb and a finger with one of the fingers covering the wedge member head 45, and then squeezed. This finger pressure then presses the wedge member 35 into place.

When it is desired to free the lead end from the header 14, such as to replace the pacer 10, the wedge member 35 is simply pushed outboard from the channel. All that is required is to use any suitable implement to engage the legs 40a, 40b and then push the wedge member out, pin 38 included. A minimal amount of force is required.

Referring now to FIGS. 6 to 11 and the second embodiment of the invention, a header 50 is shown which is adapted for use with two leads. The lead ends are arranged in side-by-side fashion in the header 50. A locking mechanism housing 51 accordingly has two rigid clear plastic tubes 52a, 52b which define bores 53a, 53b in which the lead ends are received. The tubes 52a, 52b are on a base 53, which is likewise made of the same rigid clear plastic. Both the tubes and the base are formed integrally in the same molding operation.

A channel 55 runs completely through the base 54 and is orthogonal to the longitudinal axes of the tubes 52a, 52b. As in the first embodiment, the channel 55 intersects each of the tubes along an off-axis chordal portion, i.e., roughly tangentially. A side of each of the two lead ends thus extends into the channel 55 (e.g. FIGS. 6 and 10).

A pair of identical wedge members 60a, 60b are received in the channel 55, one in each end. Each has a lead engaging surface for fixing a respective lead end in place in the same manner as described with regard to the first embodiment. This surface is accordingly contoured like that of the wedge member of the first embodiment, with a first upraised portion 61, a concave depression 62 and a second upraised portion 63.

Each of the wedge members 60a, 60b has an elongated body portion 65. It will be noted that the part of the wedge member having the contoured surface is at the outboard end of this portion 65, and is offset from its longitudinal axis (best seen in FIGS. 8 and 9). An overhang is thus created by this offsetting.

Two longitudinally spaced apart detents 66 and 67 are formed on the upward surface of the elongated portion 65. These engage seriatim with a respective boss 68 formed on the sidewall of the channel 55. For instance, boss 68 would first engage in the detent 66 when the wedge member is initially inserted into the channel. It would then engage in the detent 67 when the wedge member is fully inserted (FIG. 10). The seating of the leads within the concave portions of the wedge members along with the engagement of the wedge members with the channel sidewalls thus assures that the wedge member will not be inadvertently dislodged.

Each wedge member 60a, 60b has a head 74 which abuts against the outside of the channel 55 opening. An aperture 75 is formed through the head 74 which opens beneath the overhang. Any suitable implement can be inserted through this aperture 75 to thereby engage the inboard end of the opposite wedge member in order to push that member out of the channel 55 and release its lead end.

In use, both of the wedge members 60a, 60b are inserted into opposite ends of the channel 55 to the point where the detents 66 engage with the bosses 68. The lead ends are then inserted into the bores 53a, 53b and the pins of the leads coupled with a respective terminal. The pacer is then grasped between the thumb and another finger with each finger overlying a head 74 of a wedge member, and squeezed. This finger pressure presses the two wedge members 60a, 60b all the way into the channel 55, thereby locking the two lead ends in place.

Another embodiment of the invention is diagrammatically illustrated in FIGS. 12 and 13. This embodiment uses a wedge member 80 that is rotated to fix a lead 24 in place, rather than a wedge member such as wedge member 35 that is pressed into a channel.

Wedge member 80 has a body portion 81 which is roughly semi-cylindrical in shape. A cam surface 82 is formed along one edge of the body portion 81. The wedge member 80 is completed by a screw head 83.

Wedge member 80 is received in a channel 84 having a circular cross-section, with the head 83 of the wedge member fitting within an enlarged portion of the channel. A lead 24 can be freely inserted in a lead channel 85 that intersects with the wedge member channel 84 when the wedge member is oriented with its body portion 81 below the intersection of the channels. The wedge member is then rotated via the screw head 83 to engage the cam surface 82 with the lead 24 and wedge the latter in place against the sidewall of channel 85.

Thus, while the invention has been described in connection with certain presently preferred embodiments, those skilled in the art will recognize many modifications of structure, arrangement, portions, elements, materials, and components which can be used in the practice of the invention without departing from the principles of this invention.

What is claimed is:

1. A tissue stimulator comprising:
   a housing having therein means for generating electrical pulse, and a source of electrical energy connected to said pulse generating means;
   at least one electrical conductor extending between the tissue to be stimulated and said housing, each said at least one conductor having an electrode at one end for attachment to the tissue to be stimulated and a lead at the other end;
   at least one bore in said housing adapted to receive therein a respective lead and electrical contact means located at one end of each said bore and electrically connected to said pulse generating means, each said bore having a longitudinal axis; and
   locking means for fixing said conductor lead end against withdrawal from said bore including a channel transversely intersecting said bore off-axis, and at least one wedge member slidingly received in said channel for axial movement therealong to engage a side of said conductor adjacent said lead end and wedge said conductor in place within said bore.

2. The tissue stimulator of claim 1 wherein each said at least one conductor has a lead end with a circular cross-section; and each said wedge member has at least one concavity formed thereon within which a respective one of said at least one conductors seat.

3. The tissue stimulator of claim 1 wherein each said at least one conductor has a lead end with a circular cross-section and a resilient covering; and each said wedge member is rigid having a first end, a second end and at least one concavity formed therebetween within which a respective one of said at least one conductors seat, said first end passing beyond each said conductor by deforming said conductor lead end covering with said conductor then seating in said respective concavity to thereby be fixed within said bore and said wedge member being secured against removal by said seated conductor.

4. The tissue stimulator of claim 1 wherein each said conductor lead end has a circular cross-section and a resilient covering; each said bore being sized slightly larger in diameter than said respective conductor lead end for a snug fit with said conductor lead end; each said wedge member having a conductor engaging surface comprised of a first upraised portion, at least one concave portion and a second upraised portion, each said wedge member being slidable in said channel from an unlocked position wherein each said conductor lead end can be freely inserted into said respective bore, to a locked position wherein each said wedge member is moved inwardly relative to said bore with said first upraised portion camming said conductor into tight frictional engagement with a sidewall defining said bore and deforming said resilient covering, said conductor passing over said first upraised portion and seating in said respective concave portion, each said conductor thereby being fixed in said bore against removal, each said wedge member being fixed in said channel against removal by the seating of said conductor in said concave portion between said two upraised portions.

5. The tissue stimulator of claim 1 wherein said channel extends through said housing, each said at least one wedge member received in one end of said channel and removed from said channel be inserting an implement in the opposite end of said channel and pushing said wedge member out.

6. The tissue stimulator of claim 5 wherein each said wedge member has an inboard end which is first inserted in said channel and an outboard end, said inboard end having a pair of legs, and further including means receivable between said legs for spreading said legs apart and into tight engagement with sidewalls defining said channel.

7. The tissue stimulator of claim 5 further comprising a cavity in each said at least one wedge member defining a pair of legs a pin having an enlarged head with said head seating in said cavity to spread said legs thereby fixing said wedge in said channel.

8. The tissue stimulator of claim 7 further comprising a boss formed on each of said legs and received in a corresponding detent formed in said channel sidewalls when said wedge member is inserted into said channel prior to locking said conductor lead end.

9. The tissue stimulator of claim 3 wherein said channel extends through said housing, said wedge member has an inboard end which is first inserted in said channel and an outboard end, said inboard end having a pair of legs, and further including means receivable between said legs for spreading said legs apart and into tight engagement with sidewalls defining said channel.

10. The tissue stimulator of claim 4 wherein said channel extends through said housing, said wedge member has an inboard end which is first inserted in said channel and an outboard end, said inboard end having a pair of legs, and further including a pin which is received between said legs and spreads said legs apart and into engagement with sidewalls defining said channel, said pin having an enlarged head which seats in a cavity formed between said legs to fix said pin in place, each of said legs having a boss formed thereon which is received in a corresponding detent formed in said channel sidewalls when said wedge member is in said unlocked position.

11. The tissue stimulator of claim 1 wherein said tissue stimulator further comprises a pair of conductors and means for coupling both of said conductors to said pulse generating means including a pair of bores within which said conductor lead ends are respectively received, said locking means further comprising a pair of wedge members received in said channel each of which engages a side of a respective conductor and wedges it in place within its respective bore.

12. The tissue stimulator of claim 11 wherein said channel extends through said housing, said wedge members being received in opposite sides of said channel.

13. The tissue stimulator of claim 12 wherein each said wedge member has a concavity formed thereon within which said lead end seats.

14. The tissue stimulator of claim 12 wherein said conductor lead end has a circular cross-section and a resilient covering, and each said wedge member is rigid with a lead engaging surface having a first end, a second end and a concavity formed therebetween within which a respective lead seats, said first end passing beyond a respective lead by deforming said conductor lead end covering with said conductor lead end then seating in said concavity, said conductor lead end thereby being fixed within its respective bore and said wedge member being secured against removal by said seated conductor.

15. The tissue stimulator of claim 14 wherein each wedge member has a detent formed thereon which engages with a respective boss formed within said channel when said wedge member is fully inserted in said channel.

16. The tissue stimulator of claim 14 wherein each wedge member has an inboard end which is first inserted in said channel and an outboard end, a head being formed at its outboard end which is flush with said housing when said wedge member is fully inserted in said channel, each head having an aperture formed therein through which an implement can be inserted to contact the inboard end of the other wedge member to thereby push the other wedge member out of the channel to free its respective conductor.

17. The tissue stimulator of claim 12 wherein each wedge member is rigid having an elongated body portion with an inboard end which is first inserted in said channel and an outboard end, and a conductor engaging surface, said conductor engaging surface being comprised of a first upraised portion, a concave portion and a second upraised portion, said wedge member being slidable in said channel from an unlocked position wherein said conductor lead end can be freely inserted into said bore to a locked position wherein said conductor lead end is seated in said concave portion, said wedge member being moved inwardly relative to said bore from said unlocked to said locked position with said first upraised portion camming said conductor into tight frictional engagement with a sidewall defining its respective bore and deforming said resilient covering, said conductor then passing over said first upraised portion and seating in said concave portion, said conductor engaging surface further being laterally offset from said elongated body portion and having a top and a bottom, said elongated body portion having a detent formed thereon which engages with a respective boss formed within said channel when said wedge member is fully inserted in said channel, said elongated body portions of said wedge members slidably engaging each other along a side when inserted in said channel, each wedge member having a head formed thereon at its outboard end which is flush with said pacer housing when said wedge member is fully inserted in said channel, each head having an aperture formed therein through which an implement can be inserted to contact the inboard end of the other wedge member to thereby push the other wedge member out of the channel to free its respective conductor.

18. The tissue stimulator of claim 1 wherein the stimulator is a body implantable cardiac pacer.

19. A tissue stimulator comprising:
a housing assembly containing:
means for generating an electric pulse,
a source of electrical energy connected to said pulse generating means,
a pair of electrical conductors extending between the tissue to be stimulated and said housing assembly, each conductor having an electrode at one end for attachment to the tissue to be stimulated and a lead at the other end,
means for electrically coupling each of said leads to said pulse generating means, said electrical coupling means being located at an inner end of each of a pair of parallel bores within which a respective conductor lead end is received, each bore having a longitudinal axis, and
locking means for fixing each conductor lead end against withdrawal from said bore and including a channel transversely intersecting both of said bores off-axis, and at least one wedge member slidingly received in said channel for axial movement therealong to engage a side of a respective conductor adjacent said lead end and wedge said lead in place within its respective bore.

20. The tissue stimulator of claim 19 wherein said channel extends through said housing, said wedge members being received in opposite sides of said channel.

21. The tissue stimulator of claim 20 wherein each said wedge member has concavity formed thereon within which said lead end seats.

22. The tissue stimulator of claim 20 wherein said conductor lead ends have circular cross-sections and resilient coverings, and each said wedge member is rigid with a lead engaging surface having a first end, a second end and a concavity formed therebetween within which said lead seats, said first end passing beyond a respective lead by deforming said conductor lead end covering with said conductor then seating in said concavity, said conductor lead end thereby being fixed within its respective bore and said wedge member being secured against removal by said seated conductor.

23. The tissue stimulator of claim 22 wherein each wedge member has a detent formed thereon which engages with a respective boss formed within said channel when said wedge member is fully inserted in said channel, each wedge member further having an inboard end which is first inserted in said channel and an outboard end, a head being formed at the outboard end of each wedge member which is flush with said housing when said wedge member is fully inserted in said channel, each head having an aperture formed therein through which an implement can be inserted to contact the inboard end of the other wedge member to thereby push the other wedge member out of the channel to free its respective conductor.

24. The tissue stimulator of claim 19 wherein the stimulator is a body implantable cardiac pacer.

* * * * *